(12) United States Patent
Dabney

(10) Patent No.: US 9,700,735 B2
(45) Date of Patent: *Jul. 11, 2017

(54) MEDICAL AND VETERINARY APPLICATIONS OF LIGHT TO ANTIMICROBIAL AND ANTINEOPLASTIC CHEMICALS

(71) Applicant: Paul Dabney, Georgetown, TX (US)

(72) Inventor: Paul Dabney, Georgetown, TX (US)

(73) Assignee: Dabney Patents, L.L.C., Georgetown, TX (US)

(*) Notice: Subject to any disclaimer, the term of this patent is extended or adjusted under 35 U.S.C. 154(b) by 106 days.

This patent is subject to a terminal disclaimer.

(21) Appl. No.: 14/630,513

(22) Filed: Feb. 24, 2015

(65) Prior Publication Data

US 2016/0015999 A1 Jan. 21, 2016

Related U.S. Application Data

(63) Continuation-in-part of application No. 14/497,269, filed on Sep. 25, 2014, now Pat. No. 9,579,177, which
(Continued)

(51) Int. Cl.
*A61N 5/06* (2006.01)
*A61C 19/06* (2006.01)
(Continued)

(52) U.S. Cl.
CPC ............ *A61N 5/062* (2013.01); *A61C 19/06* (2013.01); *A61D 7/00* (2013.01); *A61M 5/14* (2013.01); *A61N 2005/063* (2013.01); *A61N 2005/0606* (2013.01); *A61N 2005/0612* (2013.01); *A61N 2005/0645* (2013.01); *A61N 2005/0647* (2013.01)

(58) Field of Classification Search
CPC ....... A61C 19/06; A61C 19/063; A61C 1/088; A61M 5/445; A61M 25/0043; A61N 5/0616; A61N 2005/0662; A61K 33/40; A61K 31/65; A61K 31/7056; A61K 47/22; A61K 31/7048; A61K 31/203; A61K 31/60

See application file for complete search history.

(56) References Cited

U.S. PATENT DOCUMENTS 8,439,674 B2 * 5/2013 Li ................ A61C 19/063
                                           433/24
8,591,229 B2 * 11/2013 Keller ............ A61C 19/063
                                           433/80
(Continued)

*Primary Examiner* — Rex R Holmes
(74) *Attorney, Agent, or Firm* — Maier & Maier, PLLC

(57) ABSTRACT

A device having medical and veterinary applications of light to antimicrobial and antineoplastic chemicals includes a solution retainer adapted to retain a therapeutic solution against a user, the therapeutic solution including an antimicrobial chemical, an antineoplastic chemical, or both; a fiber optic cable; a light termination on the fiber optic cable that provides light from the fiber optic cable to the therapeutic solution in the solution retainer; and a light source that provides a light of a predetermined wavelength to the fiber optic cable; wherein the light provides a synergistic effect in the therapeutic solution that inhibits microbial or neoplastic growth.

18 Claims, 7 Drawing Sheets

Related U.S. Application Data is a continuation-in-part of application No. 14/536,633, filed on Nov. 9, 2014, now Pat. No. 9,504,848, and a continuation-in-part of application No. 14/583,580, filed on Dec. 26, 2014.

(60) Provisional application No. 62/026,498, filed on Jul. 18, 2014.

(51) Int. Cl.
*A61D 7/00* (2006.01)
*A61M 5/14* (2006.01)

(56) References Cited

U.S. PATENT DOCUMENTS

| | | | | |
|---|---|---|---|---|
| 2009/0018424 A1* | 1/2009 | Kamath | ............ | A61B 5/14542 600/347 |
| 2014/0011162 A1* | 1/2014 | Zegarelli | ............ | A61C 13/0013 433/215 |

* cited by examiner

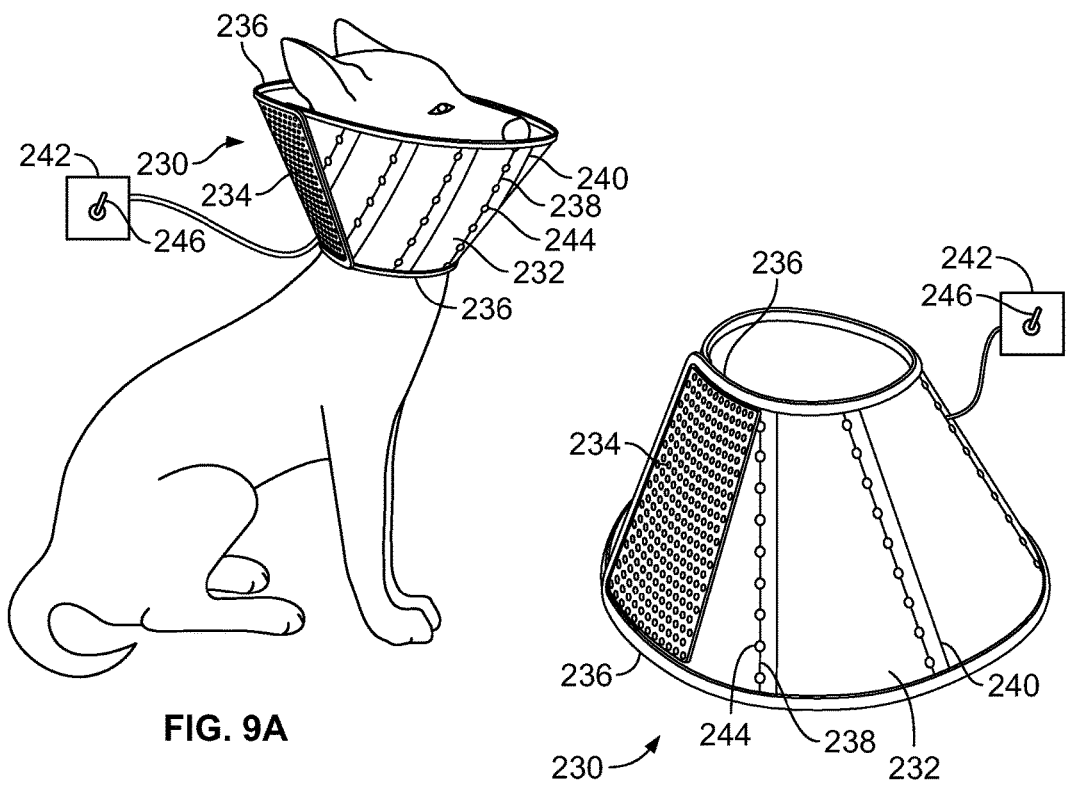
FIG. 9A
FIG. 9B
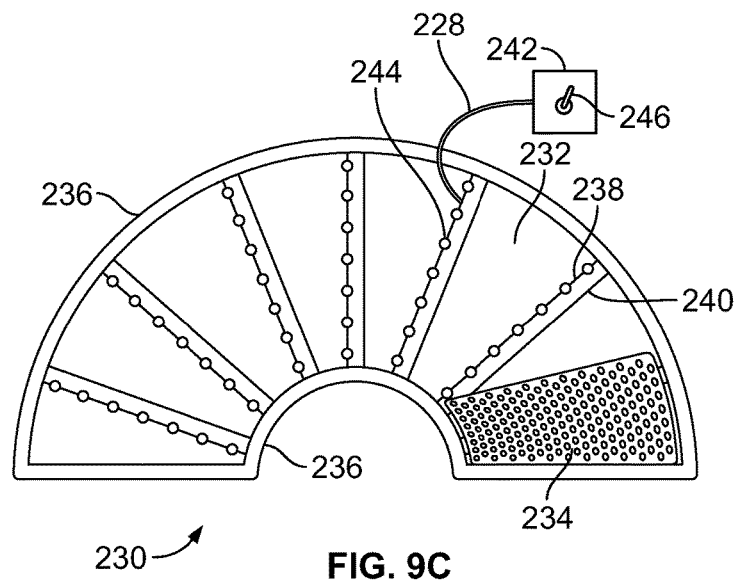
FIG. 9C

MEDICAL AND VETERINARY APPLICATIONS OF LIGHT TO ANTIMICROBIAL AND ANTINEOPLASTIC CHEMICALS

RELATED APPLICATIONS

This application claims the benefit of the filing date of U.S. Patent Application No. 62/026,498, filed Jul. 18, 2014, which is incorporated herein by reference in its entirety, U.S. patent application Ser. No. 14/497,269, filed Sep. 24, 2014, which is incorporated herein by reference in its entirety; U.S. patent application Ser. No. 14/536,633, filed Nov. 9, 2014, which is incorporated herein by reference in its entirety; and U.S. patent application Ser. No. 14/583,580, filed Dec. 26, 2014, which is incorporated herein by reference in its entirety.

BACKGROUND OF THE INVENTION

The present invention generally relates to therapy including enhancement of chemical effects with light and more specifically to medical and veterinary applications of light to antimicrobial and antineoplastic chemicals including antimicrobial and antineoplastic solutions.

Microbes exist that cause harm or disease in living tissues of humans and animals. Tumors or neoplasts such as cancer also cause harm to the tissues of humans and animals.

Light of certain wavelengths has been demonstrated to improve or "super-charge" the effects of certain pharmaceuticals or target chemicals, such as antimicrobial and antineoplastic agents, creating a synergistic effect to destroy or inhibit microbial or neoplastic growth.

It would be desirable to add light of certain wavelengths to certain antimicrobial or antineoplastic agents or both so a synergistic effect can be created to destroy or inhibit microbial growth or tumors.

SUMMARY OF THE INVENTION

In one aspect of the present invention, a device includes a solution retainer adapted to retain a therapeutic solution against a user, the therapeutic solution including an antimicrobial chemical, an antineoplastic chemical, or both; a fiber optic cable; a light termination on the fiber optic cable that provides light from the fiber optic cable to the therapeutic solution in the solution retainer; and a light source that provides a light of a predetermined wavelength to the fiber optic cable; wherein the light provides a synergistic effect in the therapeutic solution that inhibits microbial or neoplastic growth.

BRIEF DESCRIPTION OF THE DRAWINGS

FIGS. 9A-9C depict embodiments of animal covers according to the present invention.

DETAILED DESCRIPTION

Figure 1:
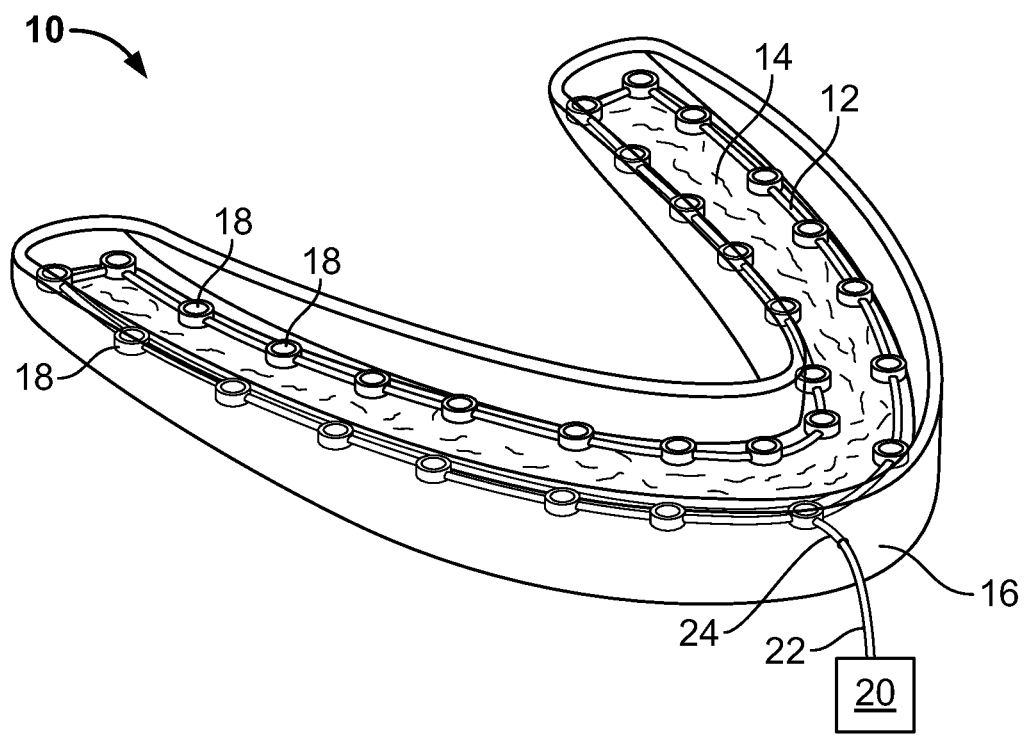
FIG. 1 depicts an embodiment of a dental device according to the present invention.

The preferred embodiment and other embodiments, which can be used in industry and include the best mode now known of carrying out the invention, are hereby described in detail with reference to the drawings. Further embodiments, features and advantages will become apparent from the ensuing description, or may be learned without undue experimentation. The figures are not necessarily drawn to scale, except where otherwise indicated. The following description of embodiments, even if phrased in terms of "the invention" or what the embodiment "is," is not to be taken in a limiting sense, but describes the manner and process of making and using the invention. The coverage of this patent will be described in the claims. The order in which steps are listed in the claims does not necessarily indicate that the steps must be performed in that order. The phrase "and/or" between two elements means the first element alone, the second element alone, or both elements together.

An embodiment of the present invention generally provides medical and veterinary applications of light to a therapeutic solution containing antimicrobial or antineoplastic chemicals.

Embodiments of a therapeutic solution may hold oxidizers, antimicrobials or antineoplastics in contact with tissues, such as a human's or animal's flesh, while the tissues and solution are simultaneously being exposed to certain wavelengths of light. Embodiments may have a component that amplifies the effect of the antimicrobial and/or antineoplastic solutions by using a certain wavelength of light. When the light is applied to the solution, the solution is "super-charged" by the light. This synergistic effect eliminates or reduces more microbes or tumors than the solution acting alone. This may be accomplished by various means including light directly from a light source, or from a light source in combination with a dental tray or other tray or container, a mask, a bandage, a horse blanket or animal covering, or a device for applying antimicrobial or antineoplastic chemicals for therapy.

Microbes exist that cause harm or disease in living tissues. By adding a light of certain wavelengths to a device that holds certain antimicrobial and/or antineoplastic agents in close proximity to tissues, a synergistic effect can be created to destroy or inhibit microbial or neoplastic growth. For example, in an oral cavity, this device could be a tray designed to cover the teeth and gingival. This tray would emit certain wavelengths of light that when combined with certain antimicrobial and/or antineoplastic solutions in the tray would cause a synergistic antimicrobial and/or antineoplastic effect. The light could be produced, for example, from a light emitting diode (LED) or laser. An external light source could be connected to the fiber optic cable in the solution holding apparatus with a fiber optic connection cable that may also include a fiber optic connection interface or plug.

Embodiments of the present invention may create another means to treat disease. Super charging antimicrobial or antineoplastic solutions with certain wavelengths of lights may cause the solutions to eliminate or reduce microbes and/or neoplastic tissue at a higher percentage than the solution alone. Embodiments may create a synergistic effect between certain wavelengths of light and antimicrobial and/or antineoplastic solutions that when applied to tissues eliminates or reduces disease causing microorganism sand or neoplastic tissue.

Embodiments of the present invention may consist of a solution-holding apparatus or medium that emits certain wavelengths of light into the solution. When this light and solution combination is applied to tissues, a synergistic effect is created that reduces or eliminates microorganisms and/or neoplastic tissue that cause disease. The essential components are 1. The solution holding apparatus 2. A light source 3. An antimicrobial solution or antineoplastic solution or both.

Embodiments may utilize blue light, or another certain predetermined wavelength of light that supercharges the solution, with an exposure from a few second to minutes. Embodiments may also use an H2O2 solution, such as a gel, with concentration of 0.3 mM or any concentration of solution that is suitable as an antimicrobial agent.

In an embodiment, for safety, a "scalding chart" might indicate that water of 130 degrees Fahrenheit is safe under an exposure of 30 seconds, but over that it causes burns. Water of 120 degrees Fahrenheit may be safe up to 5 minutes. Hydrogen peroxide (H2O2), when it is exposed to a light of 400-500 nanometers wavelength, may kill 96% of microbes in less than 20 seconds. This solution may work best at 57 degrees Celsius (134 degrees F.).

Alternate embodiments may include heating elements that warm and further super-charge the antimicrobial and/or antineoplastic solution. In embodiments, a device may contain heating or cooling components or both. In an embodiment, an antimicrobial solution may be preheated to an ideal or optimal temperature before it is exposed to synergizing light or used at a pH that may or may not vary. For example, Hydrogen peroxide may preferably be exposed to a light of 400-500 nanometers at 57 degrees Celsius (134 degrees F.) for less than 20 seconds. Other chemicals may have different preferred temperatures and pH.

Embodiments of a device may include integrated or internal heating elements that run adjacent to the light emitting cable in the device. Embodiments of integrated heating elements may be located in only a portion of the device, such as at the bottom of a container or garment. Heating elements may draw power from the same source as the light source, such as batteries or wall power. Power may be supplied to the heating elements in the device through the fiber optic connection cable or through a power connection cable that runs alongside the connection cable.

Alternate embodiments of heating elements may be separate from the portion of the device that retains the antimicrobial solution. Separate heating elements may warm the antimicrobial solution to an optimal temperature before the solution is added to the device, such as with a heating tray or oven, or may be used to apply heat to the antimicrobial and/or antineoplastic solution in place, such as with a hot iron or wire.

Embodiments of a device may include a light emitting fiber optic cable that may expose the antimicrobial and/or antineoplastic solution to a certain wavelength of light, such as a purposefully selected wavelength or frequency of light from an LED or laser. A cover may hold the antimicrobial solution. An embodiment may include a plurality of light terminations or other light emitters on the light emitting fiber optic cable. Each light termination taps into the fiber optic cable to pipe some of the light out the end of the termination, thereby emitting light into the antimicrobial and/or antineoplastic solution. The device may be adjustable, so that the terminations can be added or moved, or the quantity and locations of the light terminations may be measured to fit an individual user. The light terminations may be located within or on the surface of the cover so that each light termination is will be positioned in a preselected location within the retainer, such as near portions of tissue to be treated. The fiber optic cable may be opaque with light emitters spaced along its length, or may be at least partially translucent to emit light along its length. A user may be a human or an animal.

In an embodiment, a fiber optic cable may connect to a light source through a fiber optic connection cable. The connection cable may enter the cover and optically connect with the fiber optic cable through a fiber optic connection interface so that the light source can be attached and removed after use. An embodiment of the interface may include a fiber optic connection cable fixed to the fiber optic cable. Another embodiment of the interface may include a socket that mates with a plug on the connection cable so that the light source can be attached and removed after use.

An embodiment may include a device with a light source and antimicrobial and/or antimicrobial solution. Embodiments may include various human or animal body or body part coverings.

An embodiment of the present invention may include a covering for a human, horse or other animal. The covering may be connected to a light source. Embodiments may contain a multitude of fiber optic terminations. Coverings may have a heating element.

Embodiments of the present invention may include:
a dental tray that retains an antimicrobial or antineoplastic solution against a user's teeth;
a medical solution retainer adapted to retain an antimicrobial or antineoplastic solution against a human user's tissue;
a bucket or container;
a bowl;
a full body suit;
an arm sleeve;
a glove;
a leg stocking;
a toe cap;
a helmet;
a catheter tube;
a medical solution retainer adapted to retain an antimicrobial or antineoplastic solution against an animal's tissue;
a blanket for horses or other animals; or
a covering for limbs or parts of an animal.

Embodiments may include a fiber optic cable that wraps around the inside surface the device. The fiber optic cable may have light terminations spaced along the fiber optic cable inside the device. An embodiment may include a heating element inside the device. The heating element may include heating wires inside the device that run adjacent to the fiber optic cable. The fiber optic cable may connect through a connection cable to a light source. A connection interface or plug may connect and release an external light source from the device. The heating element may receive power from the light source, through the same light source connection cable or through a separate power connection cable. A switch may allow the light source, the heating power, or both to be connected yet switched on or off.

To use an embodiment, a therapist may apply antimicrobial and/or antineoplastic solution to the inside of the device, then put the device on a human or animal to receive therapy. The therapist may turn on the heater or light source or both.

The figures depict example embodiments of the present invention. The invention includes medical and veterinary applications of light to antimicrobial or antineoplastic chemicals. These examples help teach how to make and use the invention, and show how the invention might be used in commercial applications.

Embodiments may include an antimicrobial and/or antineoplastic solution that is in contact with human or animal skin. This solution may be in a liquid, gel, mist, cream or other appropriate form. The solution may or may not be heated by the device. The solution may or may not adjust the pH of the solution. The device also contains a light source emitting a light of certain wavelengths which may be 400-500 nM. This light source may be hand help. The light may be in contact with the tissue or it may be held or placed within an effective distance. The combination of antimicrobial and/or antineoplastic solution and a certain wavelength of light may create a synergistic effect causing a reaction that is greater than the sum of the reaction of the components individually (a synergistic effect). Embodiments of this combination of light of a certain wavelength and an antimicrobial and/or antineoplastic solution may be utilized to treat acne, actinic keratosis, or any other skin or systemic condition or disease.

Once applied, the antimicrobial, antineoplastic, or other therapeutic chemical may be exposed to a wavelength of light that creates a synergistic effect enhancing the effectiveness of the therapeutic chemical. This synergistic effect causes a greater reduction in bacteria associated with bacteria or tumors associated with cancer than the applications of the therapeutic solution alone or the light alone.

Dental.

FIG. 1 depicts an embodiment of a dental device 10. A light emitting fiber optic cable 12 may expose the antimicrobial solution 14 to a certain wavelength of light, such as a purposefully selected wavelength or frequency of light from an LED or laser. A tray 16 may hold the antimicrobial solution 14. An embodiment may include a plurality of light terminations 18 or other light emitters on the light emitting fiber optic cable 12. Each light termination 18 taps into the fiber optic cable 12 to pipe some of the light out the top of the termination, thereby emitting light into the antimicrobial solution 14. The device may be adjustable, so that the terminations 18 can added or moved, or the quantity and locations of the light terminations 18 may be measured to fit an individual user. The light terminations 18 may be located within the tray 16 so that each light termination 18 is will be positioned between adjacent teeth or adjacent to a tooth of the user. The fiber optic cable may be opaque with light emitters spaced along its length, or may be at least partially translucent to emit light along its length. In an embodiment, the fiber optic cable 12 may connect to a light source 20 through a fiber optic connection cable 22. The connection cable 22 may enter the tray 16 and optically connect with the fiber optic cable 12 through a fiber optic connection interface 24 so that the light source 20 can be attached and removed after use. An embodiment of the interface 24 may include an aperture in a wall of the tray 16 with a fiber optic connection cable 22 fixed to the fiber optic cable 12. Another embodiment of the interface 24 may include a socket on the tray 16 that mates with a plug on the connection cable 22 so that the light source 20 can be attached and removed after use.

Container.

Figure 2:
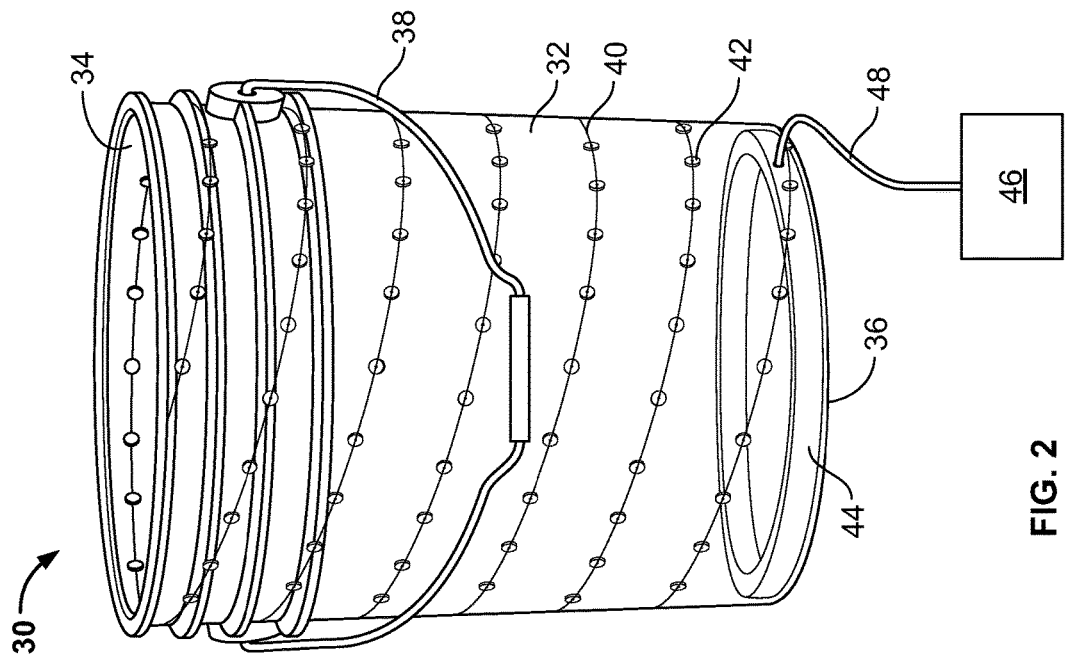
FIG. 2 depicts an embodiment of a container according to the present invention.

As depicted in FIG. 2, an embodiment of a medical device 30 may include a container 32 having a wall 34, a bottom 36, and a carrying handle 38. Embodiments may include a fiber optic cable 40 that wraps up the inner surface of the wall 34. Light terminations 42 may be located on the fiber optic cable 40 inside the container. A heating element 44 may be located around the bottom of the container 32. The fiber optic cable 40 may connect to a light source 46 through a fiber optic connection cable 48.

Bowl.

Figure 3:
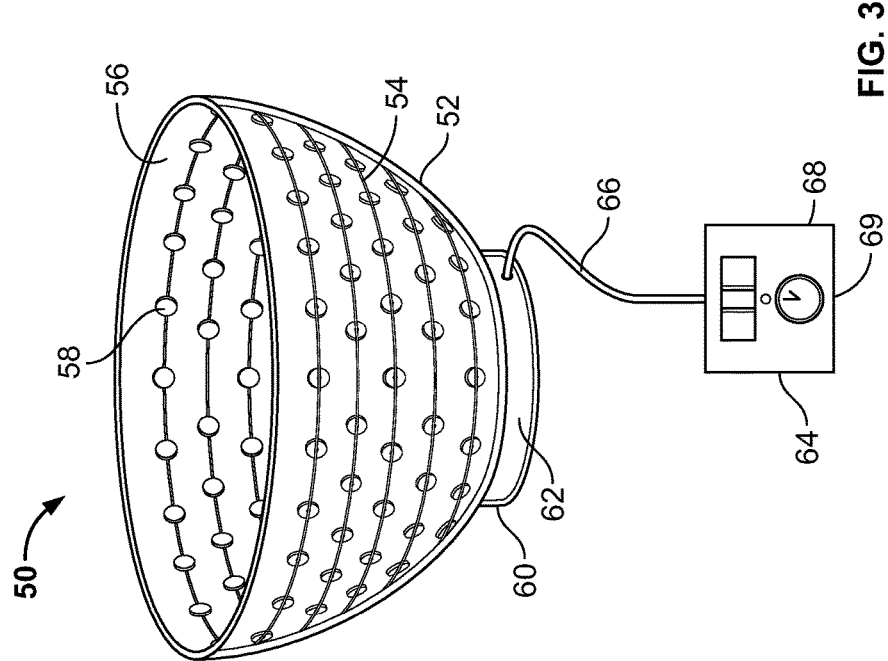
FIG. 3 depicts an embodiment of a bowl according to the present invention.

As depicted in FIG. 3, an embodiment of a medical device 50 may include a bowl 52 with a fiber optic cable 54 that wraps around an inside surface 56 of the bowl 52. The fiber optic cable 54 may have light terminations 58. Embodiments may have a base 60, which may contain a heating element 62. The fiber optic cable 54 may connect to a light source 64 through a fiber optic connection cable 66. The light source 64 may include an off/off switch 68 or a timer control 69.

Full Body Suit.

Figure 4:
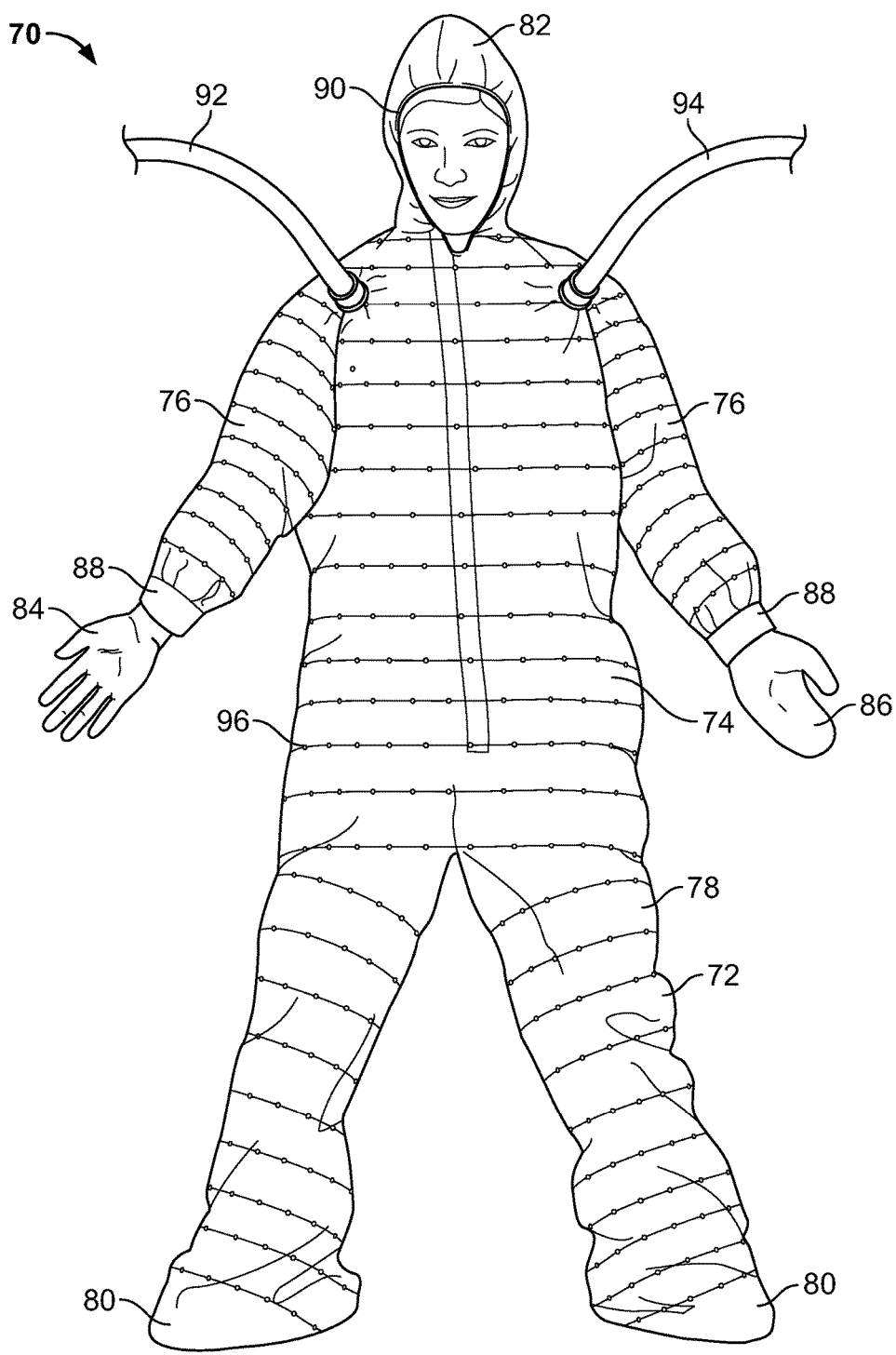
FIG. 4 depicts an embodiment of a full body suit according to the present invention.

As depicted in FIG. 4, an embodiment of a medical device 70 may include a full body suit 72 having an integrated torso portion 74, sleeves 76, pants 78, feet 80, and a hood 82, and removable gloves 84 or mittens 86. The sleeves 76 may have cuffs 88 to tighten against the user's wrists. The hood 82 may have elastic portions 90 to tighten against the user's face. Embodiments may include an input tube 92, such as on one shoulder of the torso portion 74, and an exhaust tube 94 on the opposite shoulder of the torso portion 74. Embodiments may include a fiber optic cable 96 spaced along the inner fabric of the suit 72. Light terminations 98 may be located on the fiber optic cable 96 inside the suit 72. A heating element may be embedded within the fabric of the suit 72. The fiber optic cable 96 or heating element or both may connect to a light source through a fiber optic connection cable.

Garments.

Figure 5A:
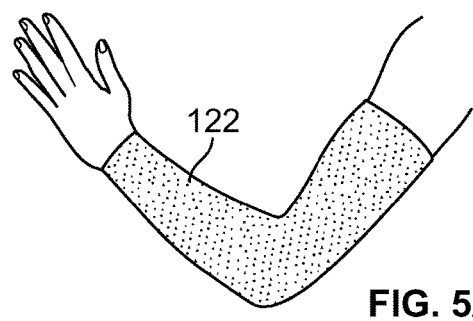
FIGS. 5A-5E depict embodiments of garments according to the present invention.
Figure 5B:
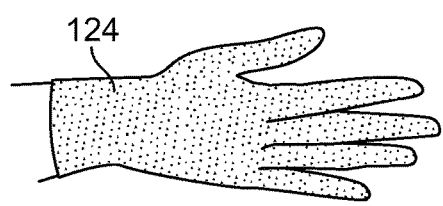
Figure 5C:
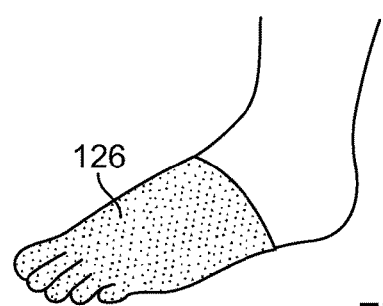
Figure 5D:
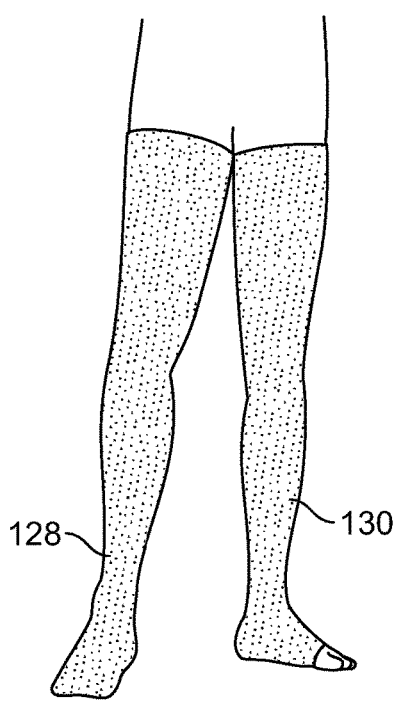
Figure 5E:
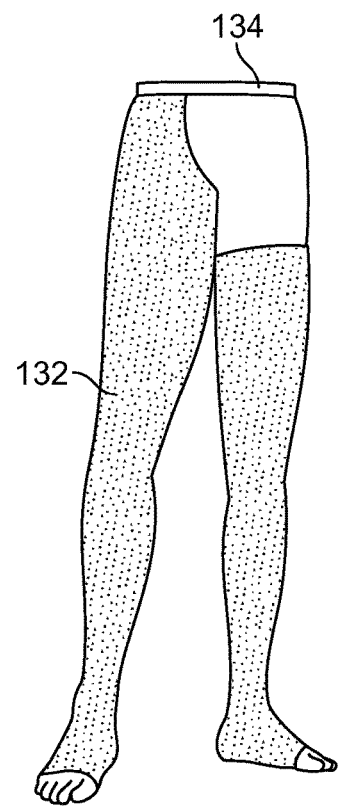

FIGS. 5A, 5B, 5C, 5D and 5E depict embodiments of medical devices including garments to carry light-enhanced antimicrobial solution to a user wearing the garment. FIG. 5A depicts an embodiment of an arm sleeve 122. FIG. 5B depicts an embodiment of a glove 124. FIG. 5C depicts an embodiment of a toe cap 126. FIG. 5D depicts an embodiment of a thigh-high stocking with a toe covering 128 or without a toe covering 130. FIG. 5E depicts an embodiment of a one foot stocking 132 with waist band 134.

Helmet.

Figure 6:
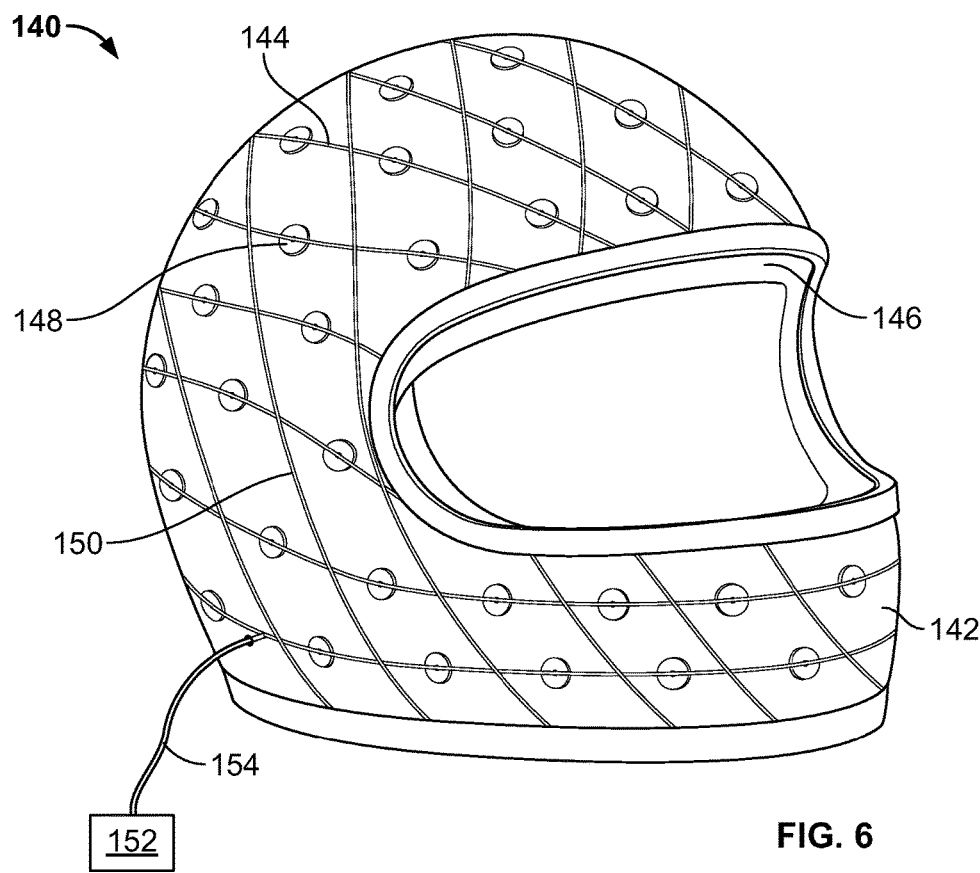
FIG. 6 depicts an embodiment of a helmet according to the present invention.

As depicted in FIG. 6, an embodiment of a medical device 140 may include a helmet 142 with a fiber optic cable 144 that wraps around an inside surface 146 of the helmet 142. The fiber optic cable 144 may have light terminations 148. Embodiments may include heating elements 150 which may include wires in a lining of the helmet. The fiber optic cable 144 may connect to a light source 152 through a fiber optic connection cable 154.

Catheter.

Figure 7:
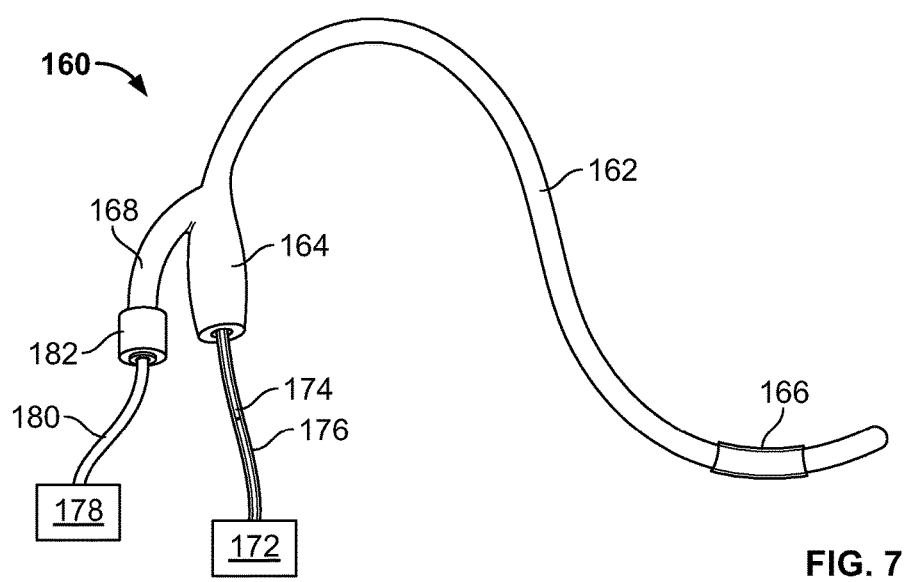
FIG. 7 depicts a catheter according to the present invention.

As depicted in FIG. 7, an embodiment of a medical device 160 may include a catheter 162 having a catheter tube 164, a mesh dispenser screen 166, and a fiber optic cable 168 having one or more light terminations 170. A heating element 172 may be external to the catheter tube 164, and may provide heated antimicrobial solution 174 through an input tube 176. A light source 178 may be connected through a fiber optic connection cable 180 to the fiber optic cable 168 with a fiber optic connection interface 182.

Horse Blanket.

Figure 8:
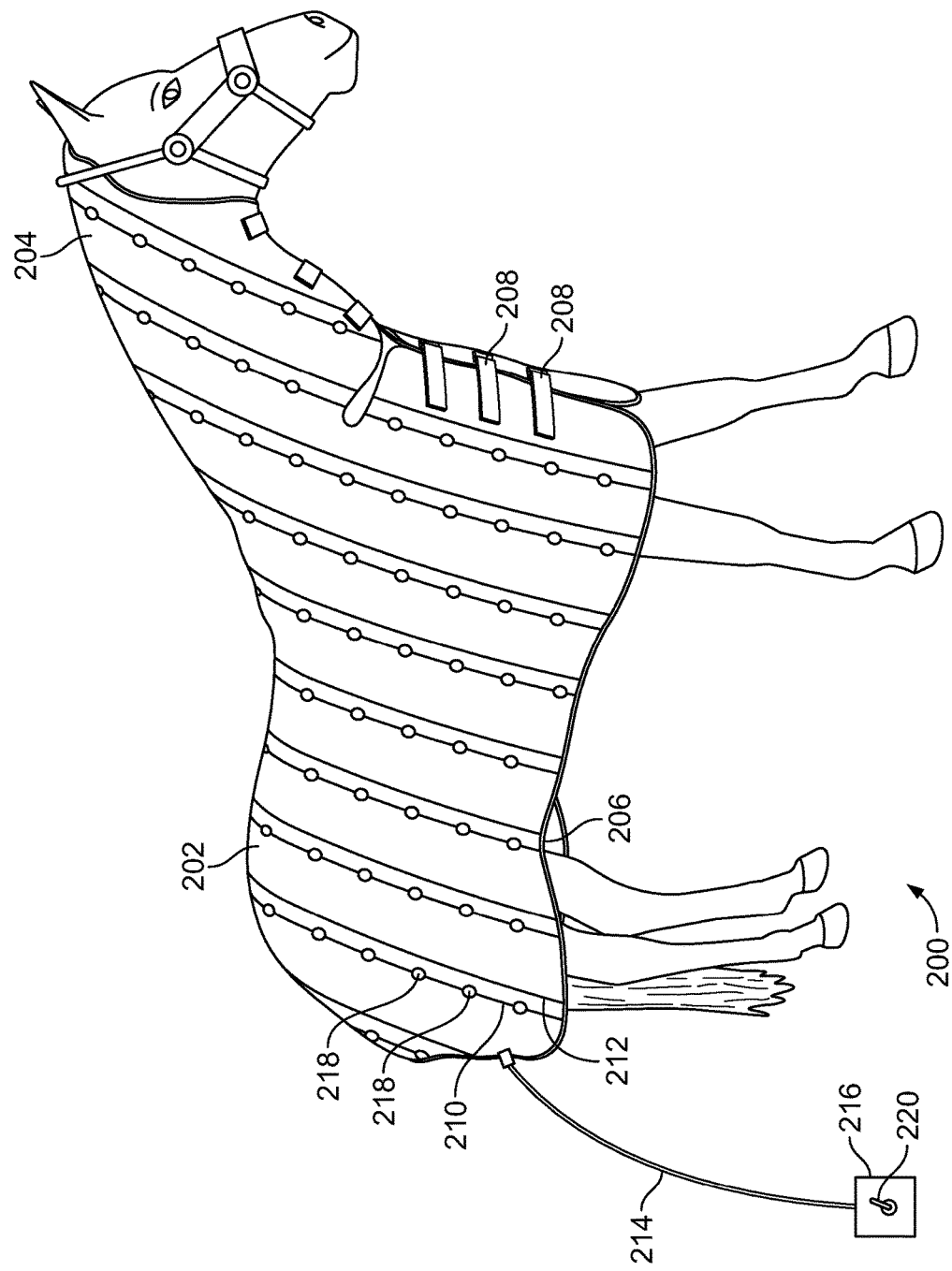
FIG. 8 depicts an embodiment of a horse blanket according to the present invention.

As depicted in FIG. 8, an embodiment of a full horse blanket 200 may include a cover portion 202, a neck portion 204, and an upper legs portion 206. A blanket 200 may include straps 208 to hold the cover closed. The blanket 200 may be coated on the inside with an antimicrobial solution or gel. Embodiments may include a fiber optic cable 210 that wraps around the inside surface the cover portion 202. Embodiments may include a heating element 212, which may include heating wires inside the cover portion 202. Embodiments may include a connection interface 214 that connects the fiber optic cable 210 to a light source 216. Light terminations 218 may be located on the fiber optic cable 210 inside the blanket 200. The light source 216 may have an on/off switch 220 or timer control.

Animal Cover.

As depicted in the embodiments of FIGS. 9A, 9B, and 9C, an animal cover 230 may include a sheet 232 of soft plastic, and an attachment mechanism 234 at one end of the sheet 232. The cover 230 may be wrapped around an animal's neck and the attachment mechanism 234 on one end of the sheet 232 may attach to the other end of the sheet 232 to form a loop. Embodiments may include a soft fabric trim 46 at the top and bottom sides, where the cover 230 rubs against the animal or other objects. The cover 230 may be coated on the inside with an antimicrobial solution or gel. Embodiments may include a fiber optic cable 238 that wraps around the inside surface the sheet 232. Embodiments may include a heating element 240, which may include heating wires inside the cover. Embodiments may include a connection interface 228 that connects the fiber optic cable 238 to a light source 242. Light terminations 244 may be located on the fiber optic cable 238 inside the blanket. The light source 230 may have an on/off switch 246 or timer control.

I claim:

1. A device comprising:
    a solution retainer adapted to retain a therapeutic solution against a user, the therapeutic solution including an antimicrobial chemical, an antineoplastic chemical, or both;
    a fiber optic cable that wraps around an inner surface of the solution retainer;
    a light termination on the fiber optic cable that provides light from the fiber optic cable to the therapeutic solution in the solution retainer; and
    a light source that provides a light of a predetermined wavelength to the fiber optic cable;
    wherein the light provides a synergistic effect in the therapeutic solution that inhibits microbial or neoplastic growth.

2. The device of claim 1, wherein the therapeutic solution includes an antimicrobial chemical that provides a synergistic effect with the light that inhibits development of microbes in the presence of light of a predetermined wavelength.

3. The device of claim 1, wherein the therapeutic solution includes an antineoplastic chemical that provides a synergistic effect with the light that inhibits development of tumors in the presence of light of a predetermined wavelength.

4. The device of claim 1, further comprising: a heating element that warms the therapeutic solution, thereby enhancing an antimicrobial or antineoplastic effect.

5. The device of claim 1, further comprising: an external light source that provides the light of a predetermined wavelength; a fiber optic connection cable that optically connects the light source with the fiber optic cable; and a socket on the solution retainer that mates with a plug on the fiber optic connection cable so that the light source may be attached and removed.

6. The device of claim 1, wherein the solution retainer includes a dental tray that retains the therapeutic solution in a cavity on a side of the tray, the fiber optic cable is retained within the tray, and the tray is shaped to hold the lighted therapeutic solution against a tooth of the user.

7. The device of claim 1, wherein: the solution retainer includes a container comprising a wall, a bottom, and a carrying handle; and the fiber optic cable wraps up an inner surface of the wall.

8. The device of claim 1, wherein: the solution retainer includes a bowl having an open top and a base beneath the bowl; wherein the fiber optic cable wraps up an inner surface of the bowl; and the fiber optic cable has a plurality of light terminations so that therapeutic solution in the bowl is lighted with light from the cable so as to substantially illuminate an item immersed in the bowl from all sides.

9. The device of claim 1, wherein: the solution retainer includes a body suit that covers at least the user's torso; and the fiber optic cable wraps up an inner surface of the suit.

10. The device of claim 1, wherein the solution retainer includes a full body suit, further comprising: an input tube to receive a therapeutic mist; an area within the suit to circulate the mist against the user; and an exhaust tube to allow the mist out of the suit.

11. The device of claim 1, wherein the solution retainer includes an arm sleeve to cover and apply light-enhanced therapeutic solution to an arm of the user.

12. The device of claim 1, wherein the solution retainer includes a glove to cover and apply light-enhanced therapeutic solution to a hand or a portion of user's hand.

13. The device of claim 1, wherein the solution retainer includes a leg stocking to cover and apply light-enhanced therapeutic solution to a leg or a portion of the user's leg.

14. The device of claim 1, wherein the solution retainer includes a toe cap to cover and apply light-enhanced therapeutic solution to one or more of the user's toes.

15. The device of claim 1, wherein the solution retainer includes a helmet to cover and apply light-enhanced therapeutic solution to the user's head.

16. The device of claim 1, the solution retainer includes a catheter tube that receives the therapeutic solution at a first end; and a mesh on the catheter tube near a second end opposite the first end, to dispense therapeutic solution into the user; wherein the light termination is located on the fiber optic cable near the mesh.

17. The device of claim 1, wherein the solution retainer includes a blanket having a cover portion shaped to cover the back, back, shoulders, sides, and rear of an animal; the fiber optic cable wraps up an inner surface of the blanket; and the fiber optic cable has a plurality of light terminations so that the therapeutic solution applied to the cover is lighted with light from the cable.

18. A method comprising:
    providing a solution retainer;
    utilizing the retainer to retain a therapeutic solution against a user, the therapeutic solution including an antimicrobial chemical,
    an antineoplastic chemical, or both;
    providing a fiber optic cable that wraps around an inner surface of the solution retainer;
    having a light termination;
    providing light from the fiber optic cable to the therapeutic solution in the solution retainer; and
    utilizing a light source to provide a light of a predetermined wavelength to the fiber optic cable that provides a synergistic effect to inhibit microbial or neoplastic growth.

* * * * *